(12) United States Patent
Feng et al.

(10) Patent No.: US 10,458,937 B2
(45) Date of Patent: Oct. 29, 2019

(54) ELECTROMAGNETIC DETECTOR FOR DETECTION OF INTERFACE CRACKS IN A PIEZOELECTRIC-PIEZOMAGNETIC LAMINATED STRUCTURE

(71) Applicant: SHIJIAZHUANG TIEDAO UNIVERSITY, Shijiazhuang (CN)

(72) Inventors: Wenjie Feng, Shijiazhuang (CN); Zhen Yan, Shijiazhuang (CN); Peng Ma, Shijiazhuang (CN); Lei Wen, Shijiazhuang (CN)

( * ) Notice: Subject to any disclaimer, the term of this patent is extended or adjusted under 35 U.S.C. 154(b) by 20 days.

(21) Appl. No.: 15/916,268

(22) Filed: Mar. 8, 2018

(65) Prior Publication Data
US 2019/0277786 A1 Sep. 12, 2019

(51) Int. Cl.
*G01N 27/02* (2006.01)
*G01R 27/26* (2006.01)
*G01R 29/22* (2006.01)

(52) U.S. Cl.
CPC ......... *G01N 27/02* (2013.01); *G01R 27/2611* (2013.01); *G01R 29/22* (2013.01)

(58) Field of Classification Search
CPC ..... G01N 27/02; G01R 29/22; G01R 27/2611
See application file for complete search history.

(56) References Cited

U.S. PATENT DOCUMENTS

| | | | | |
|---|---|---|---|---|
| 2012/0268642 | A1* | 10/2012 | Kawai | G02B 27/646 |
| | | | | 348/335 |
| 2012/0287431 | A1* | 11/2012 | Matsiev | G01N 21/31 |
| | | | | 356/306 |
| 2015/0188031 | A1* | 7/2015 | Kijima | H05B 3/0038 |
| | | | | 505/300 |

* cited by examiner

*Primary Examiner* — Tung X Nguyen
*Assistant Examiner* — Dominic E Hawkins
(74) *Attorney, Agent, or Firm* — W&K IP

(57) ABSTRACT

The present invention discloses an electromagnetic detector and a detection method for detection of interface cracks in a piezoelectric-piezomagnetic laminated structure. The electromagnetic detector for detection of interface crack in a piezoelectric-piezomagnetic laminated structure mainly comprises an eddy current magnetic probe assembly, an automatic scanning frame, a base, a carrier, a servomotor, an X-axis mobile frame driving controller, a Y-axis mobile frame driving controller, a power supply, and a main controller.

8 Claims, 9 Drawing Sheets 9-main controller
16-sensor control unit
17-host computer
18-magnetic signal extraction unit
19-magnetic signal processing unit
20-magnetic signal output unit
21-image extraction unit
22-image processing unit
23-two-dimensional image generation unit
24-image signal output unit
1101-stress extraction sensor
1102-electric displacement sensor
1103-magnetic induction intensity sensor 9-main controller
16-sensor control unit
17-host computer
18-magnetic signal extraction unit
19-magnetic signal processing unit
20-magnetic signal output unit
21-image extraction unit
22-image processing unit
23-two-dimensional image generation unit
24-image signal output unit
1101-stress extraction sensor
1102-electric displacement sensor
1103-magnetic induction intensity sensor

ELECTROMAGNETIC DETECTOR FOR DETECTION OF INTERFACE CRACKS IN A PIEZOELECTRIC-PIEZOMAGNETIC LAMINATED STRUCTURE

TECHNICAL FIELD

The present invention relates to the field of analysis technology for cracks of piezoelectric-piezomagnetic materials, in particular to an electromagnetic detector for detection of interface cracks in a piezoelectric-piezomagnetic laminated structure and a detection method.

BACKGROUND OF THE PRESENT INVENTION piezoelectric-piezomagnetic composite electromagnetic materials have electromechanical, electromagneto and magnetomechanical coupling characteristics, and have become a preferred material to produce sensors, transducers, brakes, memory and recording devices and other electronics. Due to the inherent brittleness of the materials, various defects are unavoidable during the manufacture and use of the devices. Therefore, analysis of the failure of the electromagneto composite materials due to the existence of the defects has become a hot spot for many mechanic workers.

Research on crack issue in piezoelectric-piezomagnetic composite materials and structures has important theoretical significance. Currently, many scholars have studied such problems, including interface cracks in piezoelectric-piezomagnetic materials, interface cracks in two different magnetoelectronic materials, a plurality of interlayer interface cracks in piezoelectric-piezomagnetic and magnetoelectric composite layers, and dynamic impact of single interface cracks etc.

The finite element method is one for discretizing a physical two-dimensional model into a finite set of interconnected elements for analysis and calculation. The method employs continuous function as the shape function, which requires that the shape function in the element is continuous and the material performance can not jump. Therefore, analysis of the discontinuity problems (such as inclusions and cracks) with finite element method is complicated in preprocessing, which requires a special technique for mesh generation, at the same time, its ability to analyze dynamic problems, especially moving boundary problems, is very weak. However, the extended finite element method improves the traditional finite element method based on the idea of unit decomposition, and reflects the discontinuity in the element by adding an enrichment function to the original shape function, so as to analyze the discontinuous problem more conveniently. Meanwhile, since the description to the discontinuous field is completely independent of the boundary of the mesh, it is not necessary to rely on the mesh generation method, this method has great advantages in dealing with the fracture problem.

Accordingly, it is very important to apply the extended finite element method to the analysis of interface cracks in magnetoelectric composites, especially after detecting the structure with a detector, the finite element mesh is divided according to the geometric shape of the structure, and a certain algorithm is applied to calculate the stress, electric displacement and magnetic induction intensity factor at the structure crack, which will be very advantageous to the analysis of the force at the structure crack and provide strong data support for the failure determination of the interface crack of the electromagnetic materials. However, in the prior art, there is no complete method for combining crack detection with extended finite element numerical simulation to analyze fracture characteristics of an interface crack of a magnetoelectric material.

SUMMARY OF PRESENT INVENTION

The invention designs an electromagnetic detector for an interface crack detection of a piezomagnetic-piezoelectric laminated composite material and provides an extended finite element method for further analyzing the interface crack and crack tip characteristics.

The technical solution of the present invention is as follows:

An electromagnetic detector for detection of an interface crack in a piezoelectric-piezomagnetic laminated structure, mainly comprising an eddy current magnetic probe assembly, an automatic scanning frame, a base, a carrier, a servomotor, an X-axis movable frame driving controller, a Y-axis movable frame driving controller, a power supply, and a main controller; the carrier is located on the base with a permanent magnet arranged between the carrier and the base, the automatic scanning frame is located above the carrier, the power supply supplies power for the servo motor; the automatic scanning frame is provided on the upper part with a guide rail I, a guide rail II, an X-axis movable frame and a Y-axis movable frame; the servo motor is connected to the X-axis movable frame and the Y-axis movable frame via the X-axis movable frame driving controller and the Y-axis movable frame driving controller, respectively; each of the guide rails I and the guide rails II is arranged in two, with two guide rails I are arranged respectively on two long sides of the automatic scanning frame, and two guide rails II are respectively arranged on two short sides of the automatic scanning frame, the X-axis movable frame is arranged perpendicular to the guide rails II and two ends of the X-axis movable frame are installed on the two guide rails II respectively, the Y-axis movable frames are in two, each of which is arranged perpendicular to the X-axis movable frame, and two ends of the two Y-axis movable frames are installed on the two guide rails I respectively, the eddy current magnetic probe assembly is arranged at the intersection of the X-axis movable frame and one of the Y-axis movable frames and is movable as the X-axis movable frame and Y-axis movable frames move, a high-speed CCD camera is arranged at the intersection of X-axis movable frame and the other Y-axis movable frame, the eddy current magnetic probe assembly and the high speed CCD camera are both connected to the main controller, the main controller is communicatively connected to a computer host, the main controller comprises a magnetic signal extraction unit, a magnetic signal processing unit, a magnetic signal output unit, an image extraction unit, an image processing unit, a two-dimensional image generating unit, and an image signal output unit, the magnetic signal extraction unit is connected with the eddy current magnetic probe assembly through a lead wire, the image extraction unit is connected to a high-speed CCD camera through a lead wire, the magnetic signal processing unit receives and processes the magnetic information extracted by the magnetic signal extraction unit and then sends the processed data to the host computer through the magnetic signal output unit; the image processing unit receives and processes the image information extracted by the image extraction unit, and then transmits the processed image information to the two-dimensional image generation unit to generate a two-dimensional image of a structure and sends data of the two-dimensional image to the computer host through the image signal output unit, a stress extraction sensor, an electric displacement sensor and a magnetic induction intensity sensor are all connected with the computer host through the sensor control unit.

With the electromagnetic detector, it can accurately detect information about the position and size of the interface cracks in the piezomagnetic laminated structure to be detected and provide accurate data information for the subsequent modeling and further ensure the accuracy of data such as stress, electric displacement and magnetic induction intensity factor obtained subsequently by expanded finite element method and other calculations.

Further, the eddy current magnetic probe assembly is consisted of a plurality of eddy current magnetic probes, each of which is wound around a coil and the coil is a copper wire. The permanent magnet is a U-shaped magnet, and the magnetic force lines generated by the U-shaped magnet just pass through the crack at the interface of the magneto-electro-elastic material to cause the generation of a leakage magnetic field due to the distorted of the magnetic field, and then the leakage magnetic field is detected by the eddy current magnetic probe, the information thus detected is transmitted to the magnetic signal extraction unit and the magnetic signal processing unit in the main controller through lead wires, magnetic signals will be transformed by the magnetic signal processing unit into corresponding crack information data, and then sent to the host computer.

As an improvement, a stepping motor is installed in each eddy current magnetic probe, which can be controlled by the main controller to rotate by 360°, such that the magneto-electro-elastic material to be detected on the carrier can be detected in all directions without any dead ends. Moreover, the height of the carrier is freely adjustable to further adapt to the detection requirements of different structures.

A method for detecting an interface crack in a magneto-electro-elastic material by using the present electromagnetic detector, mainly comprising the following steps:

(1) detecting a structure by the electromagnetic detector to, detect the position and the size of the crack, and storing the detected data result in a computer;

(2) establishing a two-dimensional model of the structure by a two-dimensional software in the computer, importing the generated two-dimensional model into finite element analysis software ANSYS 16.0, to establish a two-dimensional finite element analysis model of the structure, generating finite element mesh and inputting the crack data result detected in step (1) to determine the existence of a unit mesh with the crack;

(3) determining the unit type, enrichment nodes and enrichment manner using level set function according to the finite element analysis model established by ANSYS 16.0 in step (2) and its mesh generation;

(4) introducing a step function reflecting generalized discontinuous displacements, and a crack tip enrichment function reflecting the singularity of generalized stress at the crack tip is derived from the crack tip asymptotic field of the interface cracks in the piezomagnetic laminated structure. The displacement mode;

(5) Based on the principle of virtual work, combined with the above-mentioned extended finite element displacement model, the governing equations of mutual coupling of the magnetic, electrical and mechanical fields are deduced and the finite element equations of stiffness matrix and generalized force vector are obtained after discretization.

(6) Calculate the element stiffness matrix, divide the element with discontinuous general displacement and the element with the crack tip into several sub-regions and integrate the high-order Gauss integral rule and set the global stiffness matrix;

(7) Equivalent node loads and boundary conditions are applied to solve the corresponding displacements, potentials and magnetic potentials and their derivatives, and further the corresponding stress, electrical displacement and magnetic induction are obtained.

(8) Calculate the total energy release rate using the equivalent area fraction of path-independent J-integral using the obtained stress, electrical displacement and magnetic induction intensity; using the interaction integral technique, get the stress, electrical displacement and magnetic induction intensity factor, The resulting data is saved in a computer storage medium.

The beneficial effects of the present invention are as follows: the eddy current magnetic probe in the electromagnetic detector of the invention can detect the leakage magnetic field, the detected information about magnetic field is transmitted to the magnetic signal extraction unit and the magnetic signal processing unit in the main controller by lead wires, the magnetic signal is transformed into the corresponding crack information data by the signal processing unit and sent to the host computer so as to accurately obtain the information about position and size of the interface crack in the piezoelectric-piezomagnetic laminated material to be detected which ensures the accuracy of data such as stress, electrical displacement and magnetic induction intensity factor obtained subsequently by expanded finite element method and other calculations.

DESCRIPTION OF THE DRAWINGS

FIG. 3 (a) is a calculated schematic structural view (semi-structure), FIG. 3 (b) is a schematic view of meshing of the semi-structure;

FIG. 4 (a) is topological, FIG. 4 (b) is geometrical;

SYMBOL DESCRIPTION

1—eddy current magnetic probe assembly, 2—automatic scanning frame, 3—base, 4—carrier, 5—servomotor, 6—X-axis movable frame driving controller, 7—Y-axis movable frame driving controller, 8—power supply, 9—main controller, 10—permanent magnet, 11—guide rail I, 12—guide rail II, 13—X-axis movable frame, 14—Y-axis movable frame, 15—high speed CCD camera, 16—sensor control unit, 17—host computer, 18—magnetic signal extraction unit, 19—magnetic signal processing unit, 20—magnetic signal output unit, 21—image extraction unit, 22—image processing unit, 23—two-dimensional image generation unit, 24—image signal output unit.

DETAILED DESCRIPTION OF PREFERRED EMBODIMENTS

The present invention is further described in detail below with reference to the accompanying drawings and the embodiments so as to make the advantages of the present invention more fully demonstrated.

Figure 1:
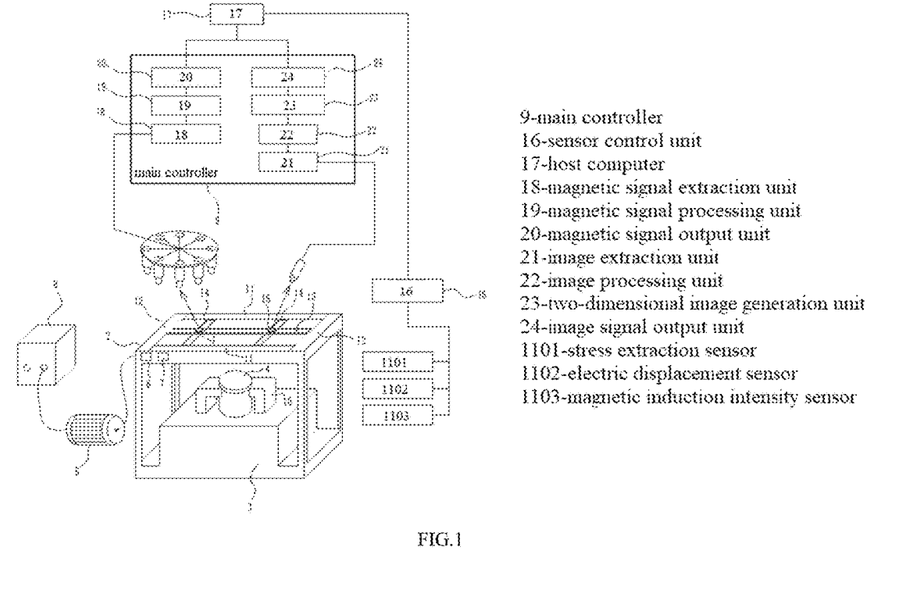
FIG. 1 is a schematic structural view of the electromagnetic detector of the present invention.

The electromagnetic detector for detection of interface crack in an electromagnetic material as shown in FIG. 1, mainly comprises an eddy current magnetic probe assembly 1, an automatic scanning frame 2, a base 3, a carrier 4, a servomotor 5, an X-axis movable frame driving controller 6, a Y-axis movable frame driving controller 7, a power supply 8, and a main controller 9, the carrier 4 is located on the base 3 with a permanent magnet 10 arranged between the carrier 4 and the base 3, the automatic scanning frame 2 is located above the carrier 4, the power supply 8 supplies power for the servo motor 5; the automatic scanning frame 2 is provided on the upper part with a guide rail I 11, a guide rail II 12, an X-axis movable frame 13 and a Y-axis movable frame 14; the servo motor 5 is connected to the X-axis movable frame 13 and the Y-axis movable frame 14 via the X-axis movable frame driving controller and the Y-axis movable frame driving controller, respectively; each of the guide rails I 11 and the guide rails 1I 12 is arranged in two, with two guide rails I 11 are arranged respectively on two long sides of the automatic scanning frame 2, and two guide rails II 12 are respectively arranged on two short sides of the automatic scanning frame 2, the X-axis movable frame 13 is arranged perpendicular to the guide rails II 12 and two ends of the X-axis movable frame 13 are installed on the two guide rails 1112 respectively, the Y-axis movable frames 14 are in two, each of which is arranged perpendicular to the X-axis movable frame 13, and two ends of the two Y-axis movable frames 14 are installed on the two guide rails 112 respectively, the eddy current magnetic probe assembly 1 is arranged at the intersection of the X-axis movable frame 13 and one of the Y-axis movable frames 14 and is movable as the X-axis movable frame 13 and Y-axis movable frames 14 move, a high-speed CCD camera 15 is arranged at the intersection of the X-axis movable frame 13 and the other Y-axis movable frame 14, the eddy current magnetic probe assembly 1 and the high speed CCD camera 15 are both connected to the main controller 9, the main controller 9 is communicatively connected to a computer host 17, the main controller comprises a magnetic signal extraction unit 18, a magnetic signal processing unit 19, a magnetic signal output unit 20, an image extraction unit 21, an image processing unit 22, a two-dimensional image generating unit 23, and an image signal output unit 24, the magnetic signal extraction unit 18 is connected with the eddy current magnetic probe assembly 1 through a lead wire, the image extraction unit 22 is connected to a high-speed CCD camera 15 through a lead wire, the magnetic signal processing unit 19 receives and processes the magnetic information extracted by the magnetic signal extraction unit and then sends the processed data to the host computer 17 through the magnetic signal output unit 20; the image processing unit 22 receives and processes the image information extracted by the image extraction unit 21, and then transmits the processed image information to the two-dimensional image generation unit 23 to generate a two-dimensional image of a structure and sends data of the two-dimensional image to the computer host 17 through the image signal output unit 24, a stress extraction sensor, an electric displacement sensor and a magnetic induction intensity sensor are all connected with the computer host 17 through the sensor control unit 16.

With the electromagnetic detector, it can accurately detect information about the position and size of the interface cracks in the piezomagnetic laminated structure to be detected and provide accurate data information for the subsequent modeling two-dimensional model for the structure and further finite element mesh generation, and further ensure the accuracy of data such as the stress, electric displacement and magnetic induction intensity factor obtained subsequently by expanded finite element method and other calculations.

The eddy current magnetic probe assembly 1 is consisted of a plurality of eddy current magnetic probes, each of which is wound around a coil and the coil is a copper wire. The permanent magnet 10 is a U-shaped magnet, and the magnetic force lines generated by the U-shaped magnet just pass through the crack at the interface of the magneto-electro-elastic material to cause the generation of a leakage magnetic field due to the distorted of the magnetic field, and then the leakage magnetic field is detected by the eddy current magnetic probe, the information thus detected is transmitted to the magnetic signal extraction unit 18 and the magnetic signal processing unit 19 in the main controller 9 through lead wires, magnetic signals will be transformed by the magnetic signal processing unit 19 into corresponding crack information data, and then sent to the host computer.

As an improvement, a stepping motor (not shown) is installed in each eddy current magnetic probe, which can be controlled by the main controller 9 to rotate by 360°, such that the electromagnetic material to be detected on the carrier 4 can be detected in all directions without any dead ends. Moreover, the height of the carrier 4 is freely adjustable to further adapt to the detection requirements of different structures.

Figure 2:
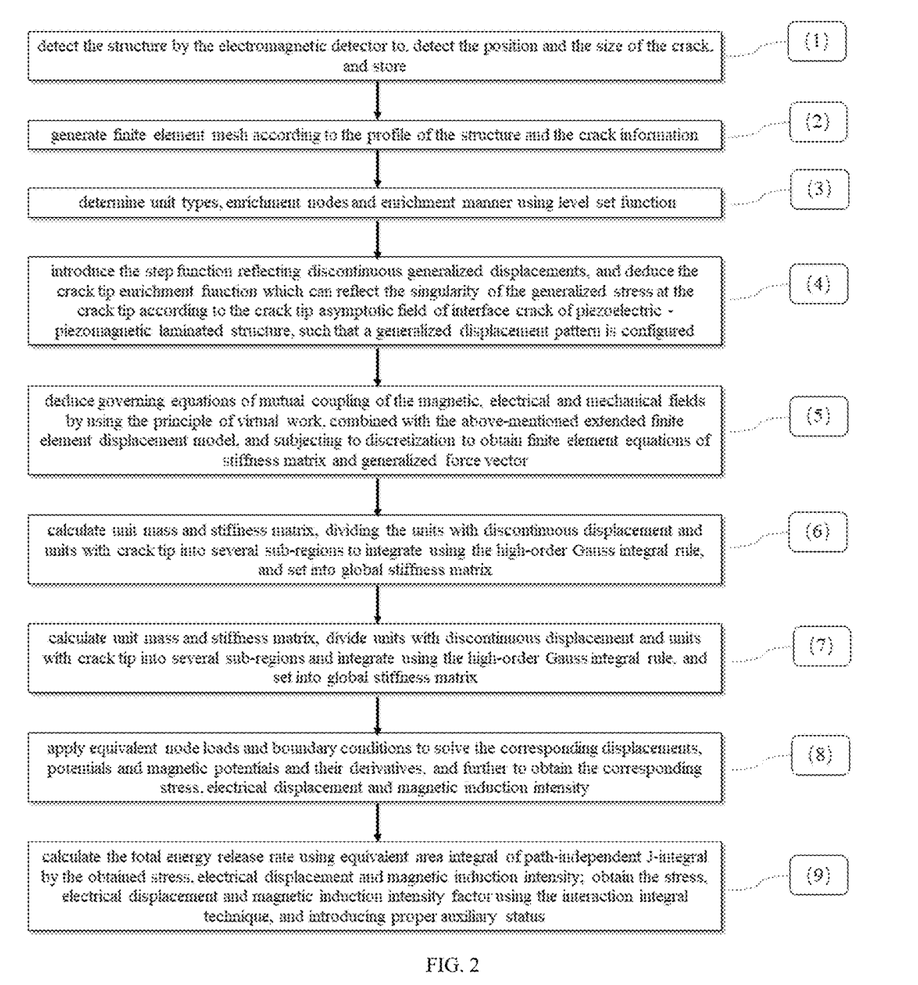
FIG. 2 is a flow chart of the detection method of the present invention.

As shown in FIG. 2, the method for detecting an interface crack in a piezoelectric-piezomagnetic laminated structure by using said electromagnetic detector mainly comprises the following steps:

(1) detecting the structure by the electromagnetic detector to, detect the position and the size of the crack, and storing the detected data result in a computer;

(2) establishing a two-dimensional model of the structure by a two-dimensional software in the computer, importing the generated two-dimensional model into finite element analysis software ANSYS 16.0 to establish a two-dimensional finite element analysis model of the structure, generating finite element mesh and inputting the crack data result detected in step (1) to determine the existence of a unit mesh with the crack;

said generating finite element mesh, is specifically: firstly, establishing a two-dimensional model of the structure containing interface crack by the two dimensional software in the computer, importing the generated two-dimensional model into finite element analysis software ANSYS 16.0 to, transform the two-dimensional model of the structure containing interface crack into a geometric shape finite element model of the structure containing interface crack, and then generating finite element mesh in the model by using the four-node quadrilateral unit, and numbering the unit as A1, A2, . . . An, where n is the total number of generated units. There are m units with cracks among said n units, and p units with crack tips, and all of the m, n and p are natural numbers. After mesh generation is finished, the unit numbers of all the units, the unit node numbers and the coordinates of each node are output by the finite element software for subsequent calculation;

(3) determining unit types, enrichment nodes and enrichment manner using level set function according to the finite element analysis model established by ANSYS 16.0 in step (2) and its mesh generation;

said determining unit types, enrichment nodes and enrichment manner using level set function, is specifically: for the structure containing an interface crack, two horizontal set functions perpendicular to each other are required to describe the crack, that is, the normal level set function $\zeta$ (x, y) and the tangential level set function $\eta$ (x, y), both of which are symbol distance functions. For the cracks with two tips, two sets of tangential level functions $\eta 1$ and $\eta 2$ are defined, and a single level set function is defined according to the law of $n=\max (\varphi 1, \varphi 2)$ on this basis. With the above conditions, the crack can be expressed by the level set functions $\zeta$ and $\eta$, that is, when $\eta=0$ and $\zeta=0$, the crack is the tip, and the unit node at the tip should be enriched by a crack tip enrichment function. When $\eta \leq 0$ and $\zeta=0$, the crack is the facial crack, and the nodes propagated by the facial crack should be enriched by a unit step function.

(4) introducing the step function reflecting discontinuous generalized displacements, and deducing the crack tip enrichment function which can reflect the singularity of the generalized stress at the crack tip according to the crack tip asymptotic field of interface crack of piezoelectric-piezomagnetic laminated structure, the tip asymptotic field indicates a distribution of the displacement field and the stress field with the crack tip as the center, and the displacement pattern is configured.

The displacement mode is:

$$u^h(x) = \sum_{i \in N} N_i(x)u_i + \sum_{j \in N^H} N_j(x)[H(f(x)) - H(f(x_j))]a_j + \sum_{k \in N^{CT}} N_k(x) \sum_{\alpha} [F_\alpha(x) - F_\alpha(x_k)]b_k^\alpha, \quad (1)$$

where i is a set of all unit nodes and j is a set of nodes of fully propagation unit, k is a set of nodes of the crack tip units; Ni is a shape function of the corresponding unit node, $u_j = [u_i, v_i, \phi_i, \varphi_i]^T$ is a displacement vector of the unit node, $\phi$ and $\varphi$ is a potential and a magnetic potential, respectively, and $a_j$, $b_k^\alpha$ is a displacement vector of the virtual node related to the step function H(x) and the facial crack enrichment function $F_\alpha(x)$, respectively. For the problem of interface crack of the transversely isotropic piezoelectric piezomagnetic laminated structure, this enrichment function can be derived as follows:

$$F^\Phi(r,\theta) = [F_1^\Phi(r,\theta), F_2^\Phi(r,\phi), F_3^\Phi(r,\theta), F_4^\Phi(r,\theta)] \quad (2)$$

where $(r,\theta)$ is the polar coordinate system with the crack tip as the coordinate origin, the superscript $\phi$ is used to distinguish the piezoelectric layer from the piezomagnetic layer, that is, when $\phi=e$, the piezoelectric material is described, while when $\phi=m$, the piezomagnetic material is described. At the same time, each component in equation (2) can be expressed as follows:

$$F_s^\Phi(r, \theta) = \sqrt{r} \sqrt{\beta_s^\Phi} [F_{s1}^\Phi(r, \theta), F_{s2}^\Phi(r, \theta), F_{s3}^\Phi(r, \theta), F_{s4}^\Phi(r, \theta), F_{s5}^\Phi(r, \theta), F_{s6}^\Phi(r, \theta),]^T \quad (3)$$

Where:

$$F_{s1}^\Phi(r, \theta) = e^{-\epsilon\psi_s^\Phi}\cos\vartheta_s^\Phi, \; F_{s2}^\Phi(r, \theta) = e^{-\epsilon\psi_s^\Phi}\sin\vartheta_s^\Phi, \; F_{s3}^\Phi(r, \theta) = e^{\epsilon\psi_s^\Phi}\cos\chi_s^\Phi \quad (4)$$

$$F_{s4}^\Phi(r, \theta) = e^{\epsilon\psi_s^\Phi}\sin\chi_s^{(m)}, \; F_{s5}^\Phi(r, \theta) = \cos(\psi_s^\Phi/2), \; F_{s6}^\Phi(r, \theta) = \sin(\psi_s^\Phi/2)$$

$$\beta_s^\Phi = \sqrt{[\cos\theta + \text{Re}(p_s^\Phi)\sin\theta]^2 + [\text{Im}(p_s^\Phi)\sin\theta]^2} \quad (5)$$

$$\psi_s^\Phi = \arg[\cos\theta + p_s^\Phi\sin\theta], \; \vartheta_s^\Phi = \epsilon\ln(r\beta_s^\Phi) + \psi_s^\Phi/2$$

$$\chi_s^\Phi = \epsilon\ln(r\beta_s^\Phi) - \psi_s^\Phi/2$$

For all the above equations s=1, 2, 3, 4; $\epsilon$ is the singularity oscillation factor of the crack tip whose value is only related to the material constants and the way that structures combined; and ps is the four feature values obtained by governing the equations.

(5) deducing governing equations of mutual coupling of the magnetic, electrical and mechanical fields by using the principle of virtual work, combined with the above-mentioned extended finite element displacement model, and subjecting to discretization to obtain finite element equations of stiffness matrix and generalized force vector.

The governing equations of the piezoelectric material and the piezomagnetic material are, respectively:

$$\begin{cases} (c_{ijks}^e \varepsilon_{ks}^e - e_{sij}^e E_s^e)_{,j} = 0, \\ (e_{iks}^e \varepsilon_{ks}^e + \alpha_{is}^e E_s^e)_{,i} = 0, \\ (\mu_{is}^e H_s^e)_{,i} = 0, \end{cases} \begin{cases} (c_{ijks}^m \varepsilon_{ks}^m - h_{sij}^m H_s^m)_{,j} = 0, \\ (\alpha_{is}^m E_s^m)_{,i} = 0, \\ (h_{iks}^m \varepsilon_{ks}^m + \mu_{is}^m H_s^m)_{,i} = 0, \end{cases} \quad (6)$$

Where the superscript e and m corresponds to the piezoelectric and piezomagnetic materials, respectively, $\varepsilon_{ij}^\Phi$, $E_i^\Phi$, $H_i^\Phi$ are stress, electric field and magnetic field, respectively; and $c_{ijks}^\Phi$, $e_{iks}^\Phi$, $h_{iks}^\Phi$, $\alpha_{is}^\Phi$, and $\mu_{is}^\Phi$ are elastic constants, piezoelectric constant, piezomagnetic constant, dielectric constant, and permeability rate, respectively.

The stiffness matrix and generalized force vector obtained by substituting the above extended finite element displacement model into the governing equation to discretize using the principle of virtual work is:

$$Ku^h = f, \quad (7)$$

Where K and f are global stiffness matrix and node force vector, respectively, which are composed of the unit stiffness matrix and the node force vector set, respectively, (6) Calculating unit mass and stiffness matrix. For units with discontinuous displacement and units with crack tip, it is required to generate several sub-regions and integrate using the high-order Gauss integral rule, and set into global stiffness matrix. For each unit, its unit mass matrix and stiffness matrix and node force vector can be expressed as $$k_{ij}^e = \begin{bmatrix} k_{ij}^{uu} & k_{ij}^{ua} & k_{ij}^{ub} \\ k_{ij}^{au} & k_{ij}^{aa} & k_{ij}^{ab} \\ k_{ij}^{bu} & k_{ij}^{ba} & k_{ij}^{bb} \end{bmatrix}, \quad (8)$$

$$f_i^e = \left\{ f_i^u \quad f_i^a \quad f_i^{b^1} \quad f_i^{b^2} \quad LL \quad f_i^{b^l} \right\}^T,$$

where u, a and b correspond to the generalized displacement vector and the generalized degree of freedom vector corresponding to the enrichment function, I is the number of crack tip enrichment function, and $$k_{ij}^{ts} = \int_{\Omega_c} (B_i^t)^T C(B_j^s) d\Omega, \ (t, s = u, a, b^\alpha), \quad (9)$$

$$f_i^t = \int_{\partial\Omega_c} S_i^t \bar{t} d\Gamma + \int_{\Omega_c} S_i^t \bar{f} d\Omega, \ (t = u, a, b^\alpha),$$

In the above two equation, $$S_i^u = N_i, S_i^a = N_i[H(f(x)) - H(f(x_i))], S_i^{b^\alpha} = N_i[F_\alpha(x) - F_\alpha(x_i)] \quad (10)$$

C is elastic matrix of materials, $\bar{t}$ and $\bar{f}$ are the generalized surface forces and physical forces, respectively, $F_\alpha$ is the first component of the enrichment function F, and the geometric matrix $B_i^H$, $B_i^a$ and $B_i^b$ can be expressed as:

$$B_i^u = \begin{bmatrix} N_{i,x} & 0 & 0 & 0 \\ 0 & N_{i,y} & 0 & 0 \\ N_{i,y} & N_{i,x} & 0 & 0 \\ 0 & 0 & N_{i,x} & 0 \\ 0 & 0 & N_{i,y} & 0 \\ 0 & 0 & 0 & N_{i,x} \\ 0 & 0 & 0 & N_{i,y} \end{bmatrix}, \quad (11)$$

$$B_i^a = \begin{bmatrix} S_{i,x}^a & 0 & 0 & 0 \\ 0 & S_{i,y}^a & 0 & 0 \\ S_{i,y}^a & S_{i,x}^a & 0 & 0 \\ 0 & 0 & S_{i,x}^a & 0 \\ 0 & 0 & S_{i,y}^a & 0 \\ 0 & 0 & 0 & S_{i,x}^a \\ 0 & 0 & 0 & S_{i,y}^a \end{bmatrix},$$

$$B_i^{b^\alpha} = \begin{bmatrix} S_{i,x}^{b^\alpha} & 0 & 0 & 0 \\ 0 & S_{i,y}^{b^\alpha} & 0 & 0 \\ S_{i,y}^{b^\alpha} & S_{i,x}^{b^\alpha} & 0 & 0 \\ 0 & 0 & S_{i,x}^{b^\alpha} & 0 \\ 0 & 0 & S_{i,y}^{b^\alpha} & 0 \\ 0 & 0 & 0 & S_{i,x}^{b^\alpha} \\ 0 & 0 & 0 & S_{i,y}^{b^\alpha} \end{bmatrix},$$

$$B_i^b = [B_i^{b^1} B_i^{b^2} L \ L \ B_i^{b^l}] \quad (12)$$

(7) subjecting the equation (4) to process by introducing the boundary conditions, to solve the generalized displacement vector of the node, and further obtain the generalized stress vector of the node.

(8) Calculating the total energy release rate using equivalent area integral of path-independent J-integral by the obtained stress, electrical displacement and magnetic induction intensity; obtaining the stress, electrical displacement and magnetic induction intensity factor using the interaction integral technique, and storing the resulting data in a computer storage medium.

The J integral can be calculated by the following equivalent area integral:

$$J = \int_A (\sigma_{ij} u_{i,1} + D_j \phi_{,1} + B_j \varphi_{,1} - W \delta_{1j}) q_{,j} dA + \quad (13)$$

$$\int_A (\sigma_{ij} u_{i,1} + D_j \phi_{,1} + B_j \varphi_{,1} - W \delta_{1j})_{,j} q dA, \ i, j = 1, 3,$$

where A is the area surrounded by the integrated contour with r as radius and the crack tip as the center, q is a weight function and is 1 in the area A, and 0 outside the area A, $\sigma_{ij}$, $D_i$, $B_i$ are stress, electric displacement, magnetic induction of each unit node, respectively, and $$W = \frac{1}{2}(\sigma_{ij} \varepsilon_{ij} - D_j E_j - B_j H_j), \ i, j = 1, 3. \quad (14)$$

For the generalized stress intensity factor of the crack, it is obtained by the method of interaction integral. J integral has the following relationship with stress, electric displacement and magnetic induction intensity factor: $J = \frac{1}{4} K^T U K$, where U is a matrix formed by material constants $$K = [K_H K_I K_D K_B]^T \quad (15)$$

For two independent equilibrium states: state 1 is the real state, state 2 is the auxiliary state, the interaction integral is:

$$2M^{(1,2)} = K_H^{(1)} K_H^{(2)} U_{11} + K_I^{(1)} K_I^{(2)} U_{22} + K_D^{(1)} K_D^{(2)}$$
$$U_{33} + K_H^{(1)} K_H^{(2)} U_{44} + (K_I^{(1)} K_H^{(2)} + K_H^{(1)} K_I^{(2)}) U_{12} +$$
$$(K_H^{(1)} K_D^{(2)} + K_D^{(1)} K_H^{(2)}) U_{13} + (K_H^{(1)} K_B^{(2)} + K_H^{(1)}$$
$$K_H^{(2)}) U_{14} + (K_I^{(1)} K_D^{(2)} + K_D^{(1)} K_I^{(2)}) U_{23} + (K_I^{(1)}$$
$$K_B^{(2)} + K_H^{(1)} K_I^{(2)}) U_{24} + (K_D^{(1)} K_B^{(2)} + K_B^{(1)} K_D^{(2)})$$
$$U_{34} \quad (16)$$

In order to facilitate calculation, in the state (2), $K_I^{(2)} = 1$ and $K_H^{(2)} = K_D^{(2)} = K_B^{(2)} = 0$, and are substituted into the equation (7), it is easy to get that the generalized stress in the true state satisfy the following relationship:

$$2\{M^{(1,H)}, M^{(1,I)}, M^{(1,D)}, M^{(1,B)}\}^T = U\{K_H^{(1)}, K_I^{(1)}, K_D^{(1)}, K_B^{(1)}\}^T \quad (17)$$

then solve it. Finally, the J integral and generalized stress intensity factor and other data are stored in the computer storage data.

EXAMPLE

Figure 3:
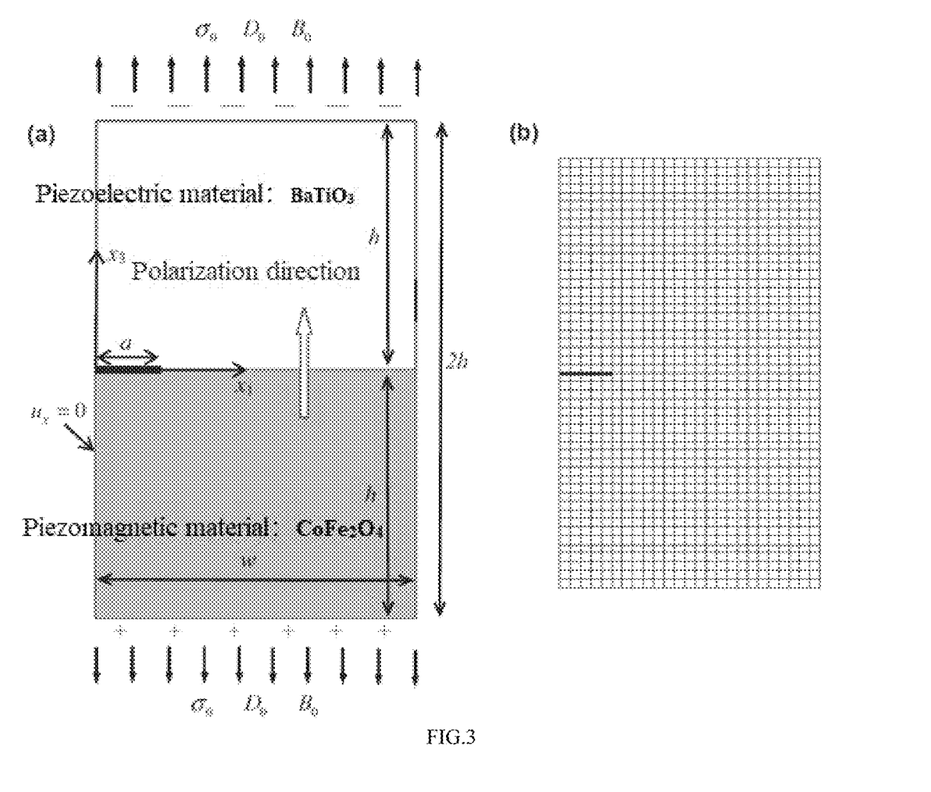
Figure 4:
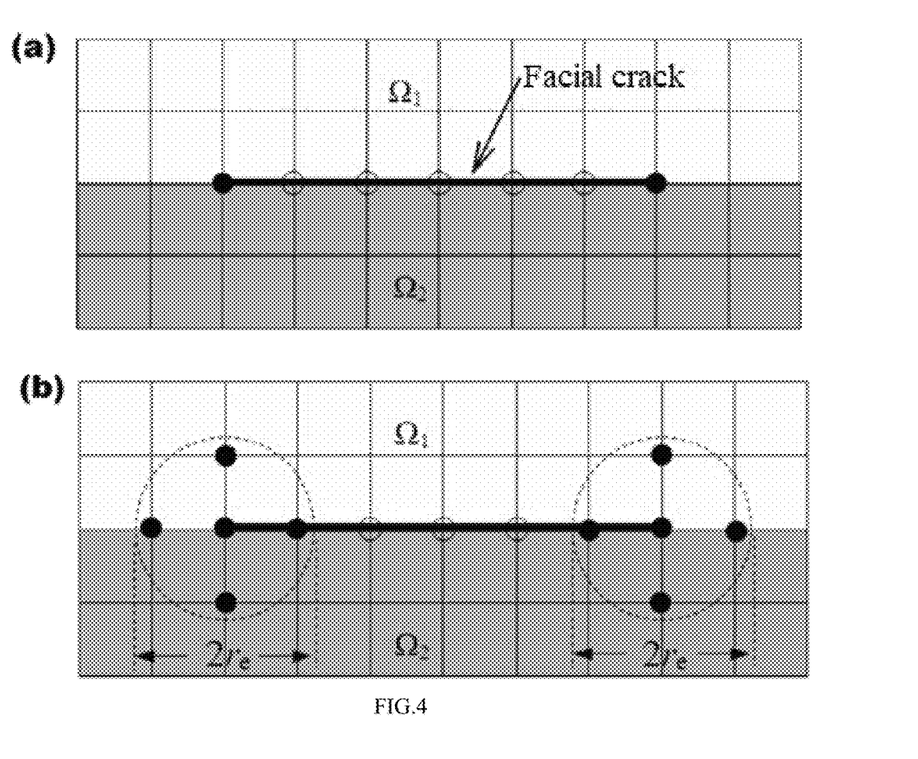

A BaTiO3-CoFe2O4 piezoelectric-piezormagnetic layered composite structure is mainly studied for the fracture behavior of interface cracks at the upper and lower outer boundaries parallel to the crack direction under the uniform force of electromagnetic coupling loads. Schematic structural view and meshing are shown in FIG. 3. The upper layer is transversely isotropic piezoelectric material BaTiO3 and the lower layer is transversely isotropic piezoelectric material CoFe2O4. For such material combination, its crack tip oscillation factor is ε=0.0315. According to the symmetry of the problem, in the calculation process, only the semi-structure is studied. FIG. 3 (a) is a schematic view of the semi-structure, the displacement u at the side of x1=0, in the direction of x1 is zero. The length of the semi-structure is w, the height is 2h and the crack length is a. There is a force electromagnetic coupling loads on the structure interface, and the polarization direction is parallel to x3 axis. FIG. 3 (b) is a schematic view for the meshing of the semi-structure, which shows a case of uniform meshing. In addition, the enrichment function is applied to enhance the points located near the facial crack and the crack tip. As shown in FIG. 4, the enrichment methods are two types of Topological and Geometrical.

(1) Analysis of Fracture Characteristics of the Interface Crack in Piezoelectric-Piezomagnetic Infinite Strip In order to verify the accuracy and stability of the calculation method used in this invention, the structure length is made large enough (w=30a) to simulate the fracture characteristics of interface cracks in the piezoelectric-piezomagnetic infinite strip under electromagnetic coupling loads. By comparing with analytic solution and classical finite element solution, the influence of meshing density, enrichment mode and enrichment function on the calculation accuracy is analyzed. Thus validating the method and finding a better state of calculation.

Figure 5:
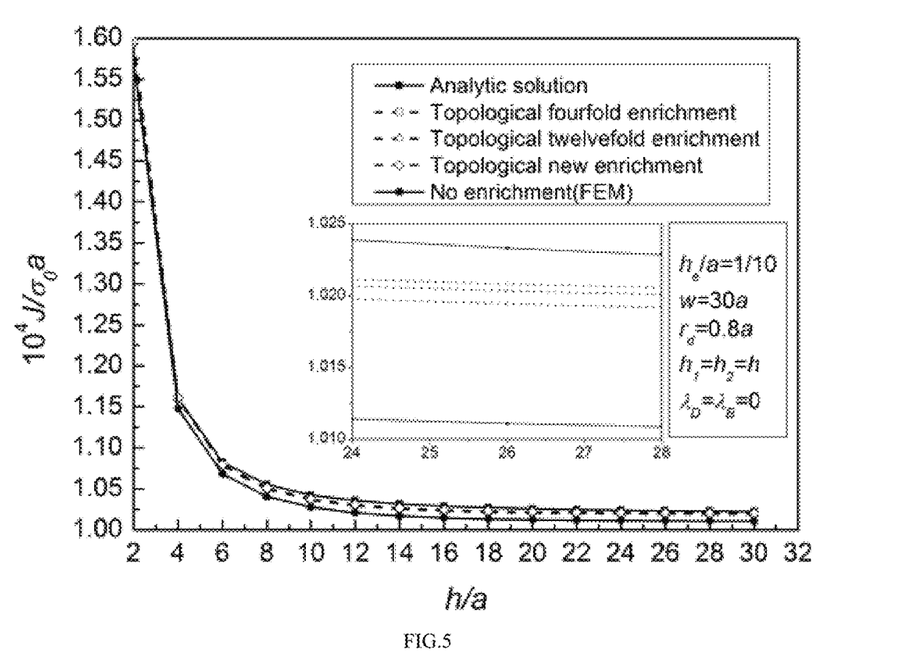
FIG. 5 shows the trend of dimensionless J integral with the height of structure.

Firstly, an overall comparison of the analytical solution, the extended finite element solution and the classical finite element solution is made. FIG. 5 describes the use of the above three methods, resulting a trend for the J integral with the change of the height of the structure. It is easily seen that the results obtained by using the extended finite element method are more approximate to the analytical solutions than that of the classical finite element method. In the meantime, the accuracy of the results calculated using the new (crack) tip enrichment function given in this patent is superior to the fourfold enrichment previously for solving internal cracks and the twelvefold enrichment for solving the elastic interface cracks.

Figure 6:
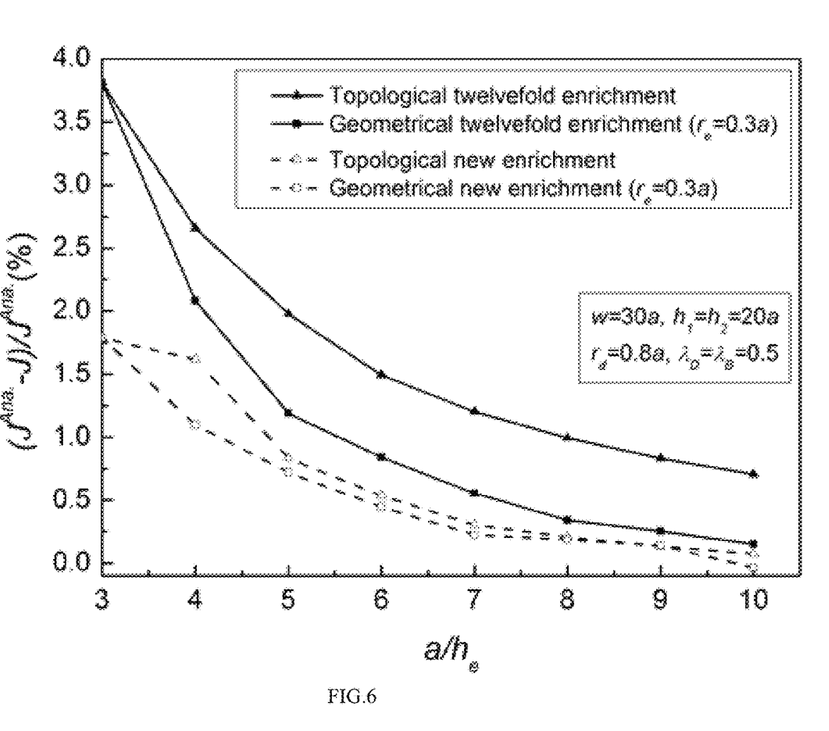
FIG. 6 is the effect of the meshing density on the accuracy of the calculation in the case of uniform meshing.

In FIG. 5, the overall structure is subject to uniformly meshing, the meshing density (i.e., the side length of each unit) is he/a=10. Next, we will further discuss the effect of the meshing density on the calculation accuracy in the case of uniform meshing. As can be seen from FIG. 6, the more dense the mesh, namely the smaller he/a (the larger a/he), the smaller the relative error of J integral, that is, the more accurate the calculation result. In addition, FIG. 6 compares the effects of two enrichments, topological enrichment and geometric enrichment, on the accuracy of the calculation. It is easily seen that under the same conditions, the calculation accuracy in geometrical enhancement is better than that of topological enrichment.

Figure 7:
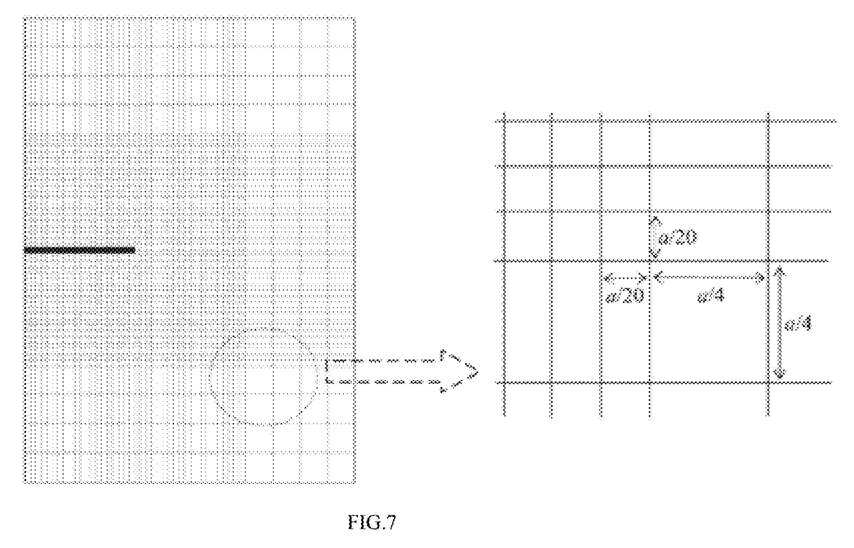
FIG. 7 is a schematic view of non-uniform meshing.

It is well known that to get a higher calculation accuracy often requires longer calculation time. In order to improve the computational efficiency and ensure the accuracy of computation, we adopt a non-uniform meshing method. A schematic view of meshing is shown in FIG. 7, wherein a relative dense is adopted near the crack and a relatively thin meshing is adopted at the location farther away from the crack. It is known from the relevant calculation data in Table 1, by using non-uniform meshing, it can effectively reduce the number of units and thus greatly improve the computational efficiency. In the meantime, since the crack near the crack has been encrypted by the non-uniform meshing, the calculation efficiency is improved while a higher calculation precision is obtained.

TABLE 1

| Mesh | Element number | Topological fourfold enrichment | Topological twelvefold enrichment | Topological new enrichment | Geometrical fourfold enrichment | Geometrical twelvefold enrichment | Geometrical new enrichment |
|---|---|---|---|---|---|---|---|
| $a/h_e = 10$ | 120000 | −0.8801 | 0.7066 | 0.0752 | −0.5746 | 0.1508 | −0.0343 |
| $a/h_{e1} = 20$, $a/h_{e2} = 3$ | 19096 | 0.7432 | 0.4532 | 0.1678 | −0.2269 | 0.1205 | 0.1027 |
| $a/h_{e1} = 20$, $a/h_{e2} = 4$ | 29184 | −0.6275 | 0.3415 | −0.1477 | −0.2381 | 0.0665 | 0.0265 |
| $a/h_{e1} = 20$, $a/h_{e2} = 5$ | 41400 | −0.5997 | 0.2893 | −0.1431 | −0.2366 | −0.0660 | −0.0259 |
| $a/h_{e1} = 20$, $a/h_{e2} = 6$ | 55744 | −0.3084 | 0.2607 | −0.1370 | −0.2335 | −0.0552 | −0.0251 |

Through the analysis of the above numerical examples, it is easily seen that the geometrical enrichment is better than the topological enrichment in the numerical accuracy. Here the influence of the size of the geometrical enrichment region on the precision of numerical results is further analyzed. It is easily seen from Table 2 that no matter what crack tip enrichment function is adopted, the larger the geometrical enrichment area is, the smaller the relative error of J integral is. At the same time, it is also obtainable from Table 2 that the new crack tip enrichment function used in this invention is superior to that of the traditional fourfold enrichment and twelvefold enrichment in calculation precision.

TABLE 2

| $r_e$ | Geometrical fourfold enrichment | Geometrical twelvefold enrichment | Geometrical new enrichment |
|---|---|---|---|
| 0.2 | −0.7358 | 0.5071 | 0.2357 |
| 0.3 | −0.6879 | 0.3406 | 0.1865 |
| 0.4 | −0.6872 | 0.2679 | 0.0674 |

Finally, we will examine the computational stability of the method used in the invention. In Table 3, a slight perturbation of the crack tip position is set, i.e., there is a deviation between the position of the crack tip and the position of the node in the computational mesh. It can be easily seen from the data in the table that under the six different enrichment strategies, the difference between the calculation error when the crack tip has deviation and the calculation error when there is no deviation is within a completely acceptable range. Therefore, the calculation method used in this invention has relatively good stability.

TABLE 3

| Δ/a | Topological fourfold enrichment | Topological twelvefold enrichment | Topological new enrichment | Geometrical fourfold enrichment | Geometrical twelvefold enrichment | Geometrical new enrichment |
| --- | --- | --- | --- | --- | --- | --- |
| 0 | 0.9950 | 0.7623 | 0.2067 | −0.6879 | 0.3406 | 0.1865 |
| −0.001 | 1.0066 | 0.7874 | 0.2241 | −0.7345 | 0.3521 | 0.1851 |
| 0.001 | 0.9864 | 0.7409 | 0.1706 | −0.7366 | 0.3268 | 0.1327 |

(2) Fracture Analysis of Interface Cracks in Piezoelectric-Piezomagnetic Plates

Figure 8:
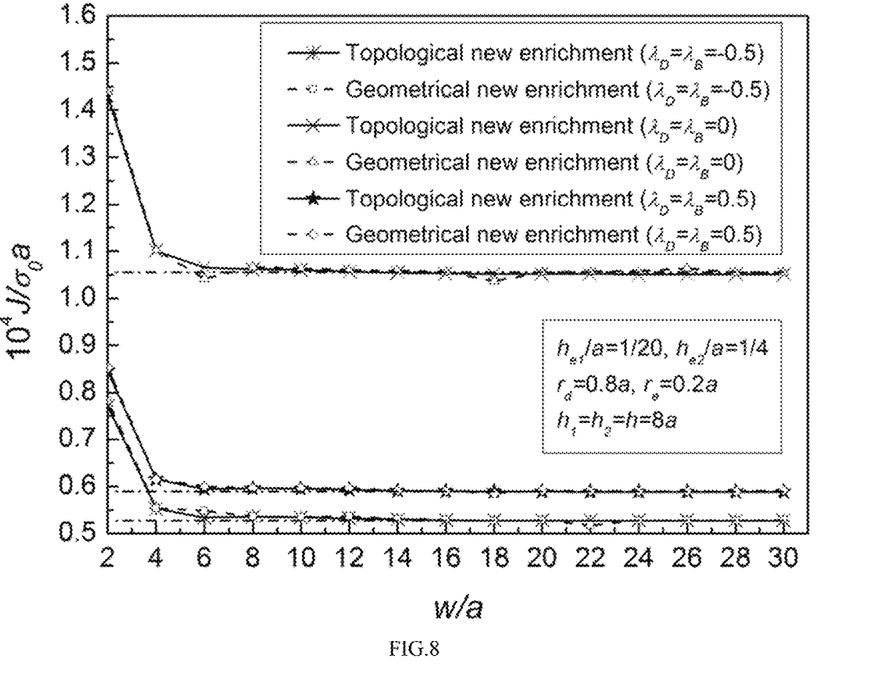
FIG. 8 shows the effect of structure width on fracture behavior under electromagnetic force loads.

Through the above analysis, it is understood the effect of factors such as network density, enrichments manner and enrichments function on the computational efficiency and accuracy. Then we use the relatively suitable computing conditions to simulate and analyze the problems that the analytical methods cannot solve. FIG. 8 reveals the influence of size effect on fracture behavior under force-electromagnetic coupling loads, where the electromagnetic loads parameter $\lambda_D = c_{11}{}'''D_0/e_{33}\sigma_0$ and $\lambda_B = c_{11}{}'''B_0/h_{33}\sigma_0$ indicates the magnitude of applied electrical displacement and magnetic field strength. It is easily seen from the figure, the smaller the size of the structure, the more dangerous the crack. When the width of the structure is eight times greater than the crack length, the J-integral is numerically the same as that of an infinitely large strip. At the same time, the application of electromagnetic loads effectively suppressed the generation and expansion of cracks.

Figure 9:
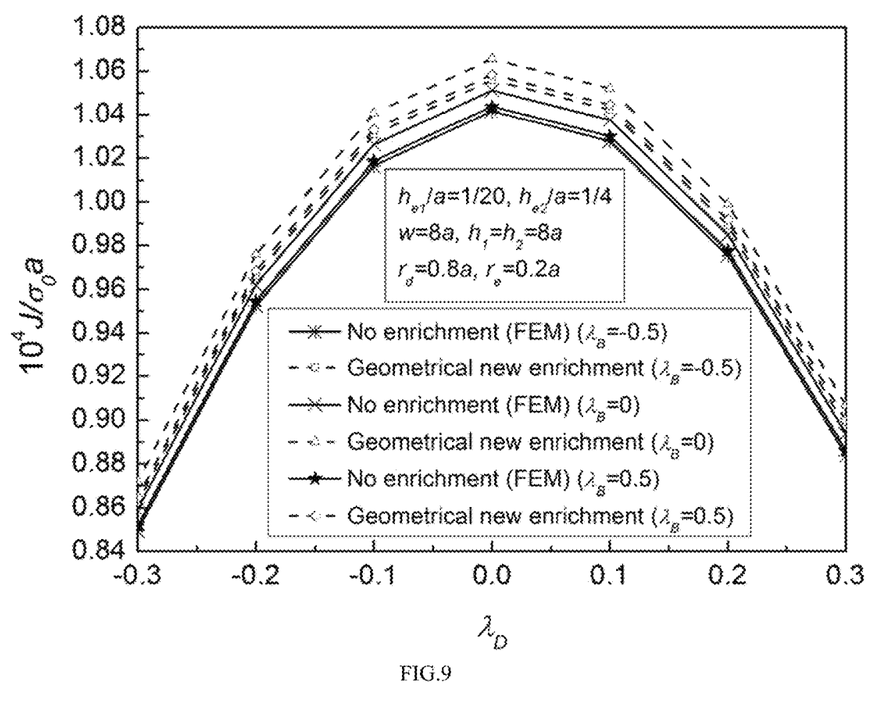
FIG. 9 is a graph of the result of effect of electromagnetic loads on the fracture characteristics of interface cracks in the piezoelectric-piezomagnetic double layer plate.

Next, we discuss the effect of electromagnetic loads on the fracture behavior of the interface cracks in the piezoelectric-piezomagnetic double-layer plate through FIG. 9. It is easily seen that, when $\lambda_B$ is fixed, J-integral increases firstly and then decrease as $\lambda_D$ increases. Similarly, when $\lambda_D$ is fixed, the J integral increases firstly and then decreases as $\lambda_B$ increases. The maximum of them are achieved with only mechanical loads.

We claim:

1. An electromagnetic detector for detection of an interface crack in a piezoelectric-piezomagnetic laminated structure, comprising an eddy current magnetic probe assembly (1), an automatic scanning frame (2), a base (3), a carrier (4), a servomotor (5), an X-axis movable frame driving controller (6), a Y-axis movable frame driving controller (7), a power supply (8), and a main controller (9);

the carrier (4) is located on the base (3) with a permanent magnet (10) arranged between the carrier (4) and the base (3), the automatic scanning frame (2) is located above the carrier (4), the power supply (8) is configured to supply power for the servo motor (5);

the automatic scanning frame (2) is provided on the upper part with a guide rail I (11), a guide rail II (12), an X-axis movable frame (13) and a Y-axis movable frame (14);

the servo motor (5) is connected to the X-axis movable frame (13) and the Y-axis movable frame (14) via the X-axis movable frame driving controller and the Y-axis movable frame driving controller, respectively;

each of the guide rails 1 (11) and the guide rails II (12) is arranged in two, with two guide rails I (11) are arranged respectively on two long sides of the automatic scanning frame (2), and two guide rails II (12) are respectively arranged on two short sides of the automatic scanning frame (2), the X-axis movable frame (13) is arranged perpendicular to the guide rails II (12) and two ends of the X-axis movable frame (13) are installed on the two guide rails II (12) respectively, the Y-axis movable frames (14) are in two, each of which is arranged perpendicular to the X-axis movable frame (13), and two ends of the two Y-axis movable frames (14) are installed on the two guide rails I (12) respectively, the eddy current magnetic probe assembly (1) is arranged at the intersection of the X-axis movable frame (13) and one of the Y-axis movable frames (14) and is movable as the X-axis movable frame (13) and Y-axis movable frames (14) move, a high-speed CCD camera (15) is arranged at the intersection of the X-axis movable frame (13) and the other Y-axis movable frame (14), the eddy current magnetic probe assembly (1) and the high-speed CCD camera (15) are both connected to the main controller (9), the main controller (9) is communicatively connected to a computer host (17), the main controller comprises a magnetic signal extraction unit (18), a magnetic signal processing unit (19), a magnetic signal output unit (20), an image extraction unit (21), an image processing unit (22), a two-dimensional image generating unit (23), and an image signal output unit (24), the magnetic signal extraction unit (18) is connected with the eddy current magnetic probe assembly (1) through a lead wire, the image extraction unit (22) is connected to a high-speed CCD camera (15) through a lead wire, the magnetic signal processing unit (19) is configured to receive and process the magnetic information extracted by the magnetic signal extraction unit and then send the processed data to the host computer (17) through the magnetic signal output unit (20);

the image processing unit (22) is configured to receive and process the image information extracted by the image extraction unit (21), and then transmit the processed image information to the two-dimensional image generation unit (23) to generate a two-dimensional image of a structure and send data of the two-dimensional image to the computer host (17) through the image signal output unit (24), a stress extraction sensor, an electric displacement sensor and a magnetic induction intensity sensor are all connected with the computer host (17) through the sensor control unit (16).

2. A method of detecting an interface crack in a piezoelectric-piezomagnetic laminated structure using the electromagnetic detector according to claim 1, comprising the steps of:

(1) detecting the structure by the electromagnetic detector to, detect the position and the size of the crack, and storing the detected data result in a computer;

(2) establishing a two-dimensional model of the structure by a two-dimensional software in the computer, importing the generated two-dimensional model into finite element analysis software ANSYS 16.0 to establish a two-dimensional finite element analysis model of the structure, generating finite element mesh and inputting the crack data result detected in step (1) to determine the existence of a unit mesh with the crack;
(3) determining unit types, enrichment nodes and enrichment manner using level set function according to the finite element analysis model established by ANSYS 16.0 in step (2) and its mesh generation;
(4) introducing the step function reflecting discontinuous generalized displacements, and deducing the crack tip enrichment function which reflects the singularity of the generalized stress at the crack tip according to the crack tip asymptotic field of interface crack of piezoelectric-piezomagnetic laminated structure, such that a generalized displacement pattern is configured;
(5) deducing governing equations of mutual coupling of the magnetic, electrical and mechanical fields by using the principle of virtual work, combined with the above-mentioned extended finite element displacement model, and subjecting to discretization to obtain finite element equations of stiffness matrix and generalized force vector;
(6) calculating unit mass and stiffness matrix, dividing the units with discontinuous displacement and units with crack tip into several sub-regions to integrate using the high-order Gauss integral rule, and setting into global stiffness matrix;
(7) applying equivalent node loads and boundary conditions to solve the corresponding displacements, potentials and magnetic potentials and their derivatives, and further to obtain the corresponding stress, electrical displacement and magnetic induction intensity;
(8) calculating the total energy release rate using equivalent area integral of path-independent J-integral by the obtained stress, electrical displacement and magnetic induction intensity; obtaining the stress, electrical displacement and magnetic induction intensity factor using the interaction integral technique, and storing the resulting data in a computer storage medium.

3. The detection method according to claim 2, wherein in said step (2), said generating finite element mesh, is specifically:
firstly, establishing a two-dimensional model of the structure containing interface crack by the two-dimensional software in the computer, importing the generated two-dimensional model into finite element analysis software ANSYS 16.0 to, transform the two-dimensional model of the structure containing interface crack into a geometric shape finite element model of the structure containing interface crack,
then generating finite element mesh in the model by using the four-node quadrilateral unit, and numbering the unit as A1, A2, . . . An,
where n is the total number of generated units,
there are m units with cracks among said n units, and p units with crack tips, and all of the m, n and p are natural numbers,
as mesh generation is finished, the unit numbers of all the units, the unit node numbers and the coordinates of each node are output by the finite element software for subsequent calculation.

4. The detection method according to claim 2, wherein said determining unit types, enrichment nodes and enrichment manner using level set function, is specifically:
for the structure containing an interface crack, two horizontal set functions perpendicular to each other are required to describe the crack, that is, the normal level set function $\zeta$ (x, y) and the tangential level set function $\eta$ (x, y), both of which are symbol distance functions;
for the cracks with two tips, two sets of tangential level functions $\eta 1$ and $\eta 2$ are defined, and a single level set function is defined according to the law of $\eta=\max (\varphi 1, \varphi 2)$ on this basis,
with the above conditions, the crack is expressed by the level set functions $\zeta$ and $\eta$, that is, when $\eta=0$ and $\zeta=0$, the crack is the tip, and the unit node at the tip should be enriched by a crack tip enrichment function. When $\eta \leq 0$ and $\zeta=0$, the crack is the facial crack, and the nodes propagated by the facial crack should be enriched by a unit step function.

5. The detection method according to claim 2, wherein the displacement mode is:

equation (1)

$$u^h(x) = \sum_{i \in N} N_i(x)u_i + \sum_{j \in N^H} N_j(x)[H(f(x)) - H(f(x_j))]a_j + \sum_{k \in N^{Cf}} N_k(x) \sum_a [F_a(x) - F_a(x_k)]b_k^a,$$

where i is a set of all unit nodes and j is a set of nodes of fully propagation unit, k is a set of nodes of the crack tip units;
Ni is a shape function of the corresponding unit node,
$u_i = [u_i, v_i, \phi_i, \varphi_i]^T$ is a displacement vector of the unit node,
$\phi$ and $\varphi$ is a potential and a magnetic potential, respectively, $a_j$, $b_k^\alpha$ is a displacement vector of the virtual node related to the step function H(x) and the facial crack enrichment function $F_\alpha(x)$, respectively, for the problem of interface crack of the transversely isotropic piezoelectric piezomagnetic laminated structure, this enrichment function is derived in equation (2) as follows:

$$F^\phi(r,\theta) = [F_1^\phi(r,\theta), F_2^\phi(r,\theta), F_3^\phi(r,\theta), F_4^\phi(r,\theta)] \quad \text{Equation (2)}$$

where (r,θ) is the polar coordinate system with the crack tip as the coordinate origin,
the superscript $\phi$ is used to distinguish the piezoelectric layer from the piezomagnetic layer, that is, when $\phi=e$, the piezoelectric material is described, while when $\phi=m$, the piezomagnetic material is described,
at the same time, each component in equation (2) is expressed as follows:

Equation (3)

$$F_s^\Phi(r, \theta) = \sqrt{r} \sqrt{\beta_s^\Phi} [F_{s1}^\Phi(r, \theta), F_{s2}^\Phi(r, \theta), F_{s3}^\Phi(r, \theta), F_{s4}^\Phi(r, \theta), F_{s5}^\Phi(r, \theta), F_{s6}^\Phi(r, \theta)]^T$$

$$F_{x1}^\phi(r,\theta) = e^{-\varepsilon \psi_s^\phi}, \cos \partial_s^\phi, F_{s2}^\phi(r,\theta) = e^{-\varepsilon \psi_s^\phi}, \sin \partial_s^\phi, F_{s3}^\phi(r,\theta) = e^{\varepsilon \psi_s^\phi}, \cos \chi_s^\phi, F_{s4}^\phi(r,\theta) = e^{\varepsilon \psi_s^\phi}, \sin \chi_s^{(m)}, F_{s5}^\gamma(r,\theta) = \cos(\psi_s^\phi/2), F_{s6}^\phi(r,\theta) = \sin(\psi_s^\phi/2) \quad \text{Equation (4)}$$

Equation (5)

$$\beta_s^\Phi = \sqrt{[\cos\theta + \text{Re}(p_s^\Phi)\sin\theta]^2 + [\text{Im}(p_s^\Phi)\sin\theta]^2}$$

-continued $$\psi_s^\Phi = \arg[\cos\theta + p_s^\Phi \sin\theta], \vartheta_s^\Phi = \varepsilon \ln(r\beta_s^\Phi) + \psi_s^\Phi/2$$

$$\chi_s^\Phi = \varepsilon \ln(r\beta_s^\Phi) - \psi_s^\Phi/2$$

for all the above equations s=1, 2, 3, or 4;
ε is the singularity oscillation factor of the crack tip whose value is only related to the material constants and the way that structures combined; and
ps is the four feature values obtained by governing the equations.

6. The detection method according to claim 2, wherein the control equation in which the piezoelectric material and the piezomagnetic material are coupled to each other is as shown in Equation (6)

Equation (6)

$$\begin{cases} (c_{ijks}^e \varepsilon_{ks}^e - e_{sij}^e E_s^e)_{,j} = 0, \\ (e_{iks}^e \varepsilon_{ks}^e + \alpha_{is}^e E_s^e)_{,i} = 0, \\ (\mu_{is}^e H_s^e)_{,i} = 0, \end{cases} \begin{cases} (c_{ijks}^m \varepsilon_{ks}^m - h_{sij}^m H_s^M)_{,j} = 0, \\ (\alpha_{is}^m E_s^m)_{,i} = 0, \\ (h_{iks}^m \varepsilon_{ks}^m + \mu_{is}^m H_s^m)_{,i} = 0, \end{cases} \quad (6)$$

Where $\varepsilon_{ij}^\Phi$, $E_i^\Phi$, $H_i^\Phi$ are stress, electric field and magnetic field, respectively;
$c_{ijks}^\Phi$, $e_{iks}^\Phi$, $h_{iks}^\Phi$, $\alpha_{is}^\Phi$ and $\mu_{is}^\Phi$ are elastic constants, piezoelectric constant, piezomagnetic constant, dielectric constant, and permeability rate, respectively.

7. The detection method according to claim 2, wherein the stiffness matrix and generalized force vector obtained by substituting the above extended finite element displacement model into the governing equation to discretize using the principle of virtual work is:

$$Ku^h = f, \quad \text{Equation (7)}$$

where K and f are global stiffness matrix and node force vector, respectively, which are composed of the unit stiffness matrix and the node force vector set, respectively, and for each unit, its unit mass matrix and stiffness matrix and node force vector are expressed as:

Equation (8)

$$k_{ij}^e = \begin{bmatrix} k_{ij}^{uu} & k_{ij}^{ua} & k_{ij}^{ub} \\ k_{ij}^{au} & k_{ij}^{aa} & k_{ij}^{ab} \\ k_{ij}^{bu} & k_{ij}^{ba} & k_{ij}^{bb} \end{bmatrix},$$

$$f_i^e = \left\{ f_i^u \quad f_i^a \quad f_i^{b1} \quad f_i^{b2} \quad LL \quad f_i^{bl} \right\}^T,$$

where u, a and b correspond to the generalized displacement vector and the generalized degree of freedom vector corresponding to the enrichment function, I is the number of crack tip enrichment function, and Equation (9)

$$k_{ij}^{ts} = \int_{\Omega_c} (B_i^t)^T C(B_j^s) d\Omega, \quad (t, s = u, a, b^\alpha),$$

$$f_i^t = \int_{\partial\Omega_c} S_i^t \bar{t} d\Gamma + \int_{\Omega_c} S_i^t \bar{f} d\Omega, \quad (t = u, a, b^\alpha).$$

in the above two equations,

Equation (10)

$$S_i^a = N_p, S_i^a = N_i[H(f(x)) - H(f(x_i))], S_i^{b\alpha} = N_i[F_\alpha(x) - F_\alpha(x_i)] \quad (10)$$

C is elastic matrix of materials, $\bar{t}$ and $\bar{f}$ are the generalized surface forces and physical forces, respectively, $F_\alpha$ is the first component of the enrichment function F, and the geometric matrix $B_i^a$, $B_i^a$ and $B_i^b$ and are expressed as:

Equation (11)

$$B_i^u = \begin{bmatrix} N_{i,x} & 0 & 0 & 0 \\ 0 & N_{i,y} & 0 & 0 \\ N_{i,y} & N_{i,x} & 0 & 0 \\ 0 & 0 & N_{i,x} & 0 \\ 0 & 0 & N_{i,y} & 0 \\ 0 & 0 & 0 & N_{i,x} \\ 0 & 0 & 0 & N_{i,y} \end{bmatrix},$$

$$B_i^a = \begin{bmatrix} S_{i,x}^a & 0 & 0 & 0 \\ 0 & S_{i,y}^a & 0 & 0 \\ S_{i,y}^a & S_{i,x}^a & 0 & 0 \\ 0 & 0 & S_{i,x}^a & 0 \\ 0 & 0 & S_{i,y}^a & 0 \\ 0 & 0 & 0 & S_{i,x}^a \\ 0 & 0 & 0 & S_{i,y}^a \end{bmatrix},$$

$$B_i^{b\alpha} = \begin{bmatrix} S_{i,x}^{b\alpha} & 0 & 0 & 0 \\ 0 & S_{i,y}^{b\alpha} & 0 & 0 \\ S_{i,y}^{b\alpha} & S_{i,x}^{b\alpha} & 0 & 0 \\ 0 & 0 & S_{i,x}^{b\alpha} & 0 \\ 0 & 0 & S_{i,y}^{b\alpha} & 0 \\ 0 & 0 & 0 & S_{i,x}^{b\alpha} \\ 0 & 0 & 0 & S_{i,y}^{b\alpha} \end{bmatrix},$$

$$B_i^b = [B_i^{b1} \quad B_i^{b2} \quad LL \quad B_i^{bi}], \quad \text{Equation (12)}$$

subjecting the equation (4) to process by introducing the boundary conditions, to solve the generalized displacement vector of the node, and further obtain the generalized stress vector of the node.

8. The detection method according to claim 2, wherein the J integral is calculated by the following equivalent area integral:

Equation (13)

$$J = \int_A (\sigma_{ij} u_{i,1} + D_j \phi_{,1} + B_j \varphi_{,1} - W\delta_{1j}) q_{,j} dA +$$

$$\int_A (\sigma_{ij} u_{i,1} + D_j \phi_{,1} + B_j \varphi_{,1} - W\delta_{1j})_{,j} q dA, \, i, j = 1, 3,$$

where A is the area surrounded by the integrated contour with r as radius and the crack tip as the center, q is a weight function and is 1 in the area A, and 0 outside the area A, $\sigma_{ij}$, $D_i$, $B_i$ are stress, electric displacement, magnetic induction of each unit node, respectively, Equation (14)

$$W = \frac{1}{2}(\sigma_{ij}\varepsilon_{ij} - D_j E_j - B_j H_j), i, j = 1, 3,$$

J integral has the following relationship with stress, electric displacement and magnetic induction intensity factor:

$$J = \frac{1}{4}K^T U K,$$

where U is a matrix formed by material constants:

$$K = [K_H K_I K_D K_B]^T \quad \text{Equation (15)}$$

for two independent equilibrium states: state 1 is the real state, state 2 is the auxiliary state, the interaction integral is:

$$2M^{(1,2)} = K_H^{(1)}K_H^{(2)}U_{11} + K_I^{(1)}K_I^{(2)}U_{22} + K_D^{(1)}K_D^{(2)}U_{33} + K_B^{(1)}K_B^{(2)}U_{44} + (K_I^{(1)}K_H^{(2)} + K_H^{(1)}K_I^{(2)})U_{12} + (K_H^{(1)}K_D^{(2)} + K_D^{(1)}K_H^{(2)})U_{13} + (K_H^{(1)}K_B^{(2)} + K_B^{(1)}K_H^{(2)})U_{14} + (K_I^{(1)}K_D^{(2)} + K_D^{(1)}K_I^{(2)})U_{23} + (K_I^{(1)}K_B^{(2)} + K_B^{(1)}K_I^{(2)})U_{24} + (K_D^{(1)}K_B^{(2)} + K_B^{(1)}K_D^{(2)})U_{34} \quad \text{Equation (16)}$$

in order to facilitate calculation, in the state (2), $K_I^{(2)}=1$ and $K_H^{(2)}=K_D^{(2)}=K_B^{(2)}=0$, and are substituted into the equation (7), to get that the generalized stress in the true state satisfy the following relationship:

$$2\{M^{(1,H)}, M^{(1,I)}, M^{(1,D)}, M^{(1,B)}\}^T = U\{K_H^{(1)}, K_I^{(1)}, K_D^{(1)}, K_B^{(1)}\}^T \quad \text{Equation (17)}$$

then solve it, finally, the J integral and generalized stress intensity factor and other data are stored in the computer storage data.

* * * * *